(12) United States Patent
Song (10) Patent No.: US 12,427,304 B2
(45) Date of Patent: Sep. 30, 2025

(54) CLOTHING FOR ELECTRICAL STIMULATION

(71) Applicant: Barun Gonghak Co., Ltd., Seoul (KR)

(72) Inventor: Hyeon Hui Song, Seoul (KR)

(73) Assignee: BARUN GONGHAK CO., LTD., Seoul (KR)

( * ) Notice: Subject to any disclaimer, the term of this patent is extended or adjusted under 35 U.S.C. 154(b) by 448 days.

(21) Appl. No.: 17/651,513

(22) Filed: Feb. 17, 2022

(65) Prior Publication Data

US 2023/0042281 A1 Feb. 9, 2023

(30) Foreign Application Priority Data

Aug. 5, 2021 (KR) .......................... 10-2021-0102957

(51) Int. Cl.
*A61N 1/04* (2006.01)
(52) U.S. Cl.
CPC .................................. *A61N 1/0484* (2013.01)
(58) Field of Classification Search
CPC ................ A61N 1/0484; A61N 1/0452; A61N 1/36014; A61N 1/10; A41D 2400/32; A41D 13/0015; A41D 1/002; A41D 13/065; A41D 17/02; A41B 2400/32; A41B 11/14; A41B 11/00
See application file for complete search history.

(56) References Cited

U.S. PATENT DOCUMENTS

| | | | |
|---|---|---|---|
| 2005/0131489 A1 | 6/2005 | Gardon-Mollard | |
| 2006/0085047 A1* | 4/2006 | Unsworth | A61N 1/36031 607/144 |
| 2016/0156282 A1* | 6/2016 | Kim | A61N 1/0484 607/61 |
| 2020/0109494 A1* | 4/2020 | Gress | D03D 15/54 |
| 2020/0177105 A1* | 6/2020 | Wang | H10N 30/8548 |
| 2022/0176112 A1* | 6/2022 | Kim | A61N 1/0496 |

FOREIGN PATENT DOCUMENTS

| | | |
|---|---|---|
| CN | 207613215 U | 7/2018 |
| KR | 20200079426 A | 7/2020 |
| WO | 2019134033 A2 | 7/2019 |
| WO | 2020073099 A1 | 4/2020 |

OTHER PUBLICATIONS

European Patent Office, Extended European Search Report Issued in Application No. 22157445.2, Aug. 9, 2022, Germany, 7 pages.

* cited by examiner

*Primary Examiner* — Niketa Patel
*Assistant Examiner* — Sebastian X Lukjan
(74) *Attorney, Agent, or Firm* — McCoy Russell LLP (57) ABSTRACT

Provided is a clothing for electrical stimulation that may apply electrical stimulation to a user's body without a separate power source and may strengthen the strength of electrical stimulation applied to the body. The clothing for electrical stimulation includes: a main body including a first clothing region clothing a user's sole and a second clothing region worn on a body part other than the user's sole; a first conductor located on an inner surface of the main body and disposed to be in contact with the user's body; and a second conductor electrically connected to the first conductor and located on an outer surface of the main body.

17 Claims, 10 Drawing Sheets

CLOTHING FOR ELECTRICAL STIMULATION

CROSS-REFERENCE TO RELATED APPLICATION

The present application claims priority to Korean Patent Application No. 10-2021-0102957, filed on Feb. 17, 2022. The entire contents of the above-listed application are hereby incorporated by reference for all purposes.

TECHNICAL FIELD

The following disclosure relates to a clothing for electrical stimulation, and more particularly, to a clothing for electrical stimulation that may apply electrical stimulation to a user's body without a separate power source and may strengthen the strength of electrical stimulation applied to the body.

BACKGROUND

Recently, various devices using electrical muscle stimulation (EMS) that directly stimulate muscles with an electric current applied from a power supply to contract muscles without a command from the brain have been developed. It has been proven to have various effects such as improving wrinkles, promoting wound and fracture healing, reducing muscle fatigue, reducing inflammation, improving blood circulation, reducing abdominal fat, and having antibacterial properties.

However, since these conventional devices using electrical muscle stimulation require an energy source such as a battery for applying electrical stimulation to the human body, they are complicated in configuration and have limitations in miniaturization.

In detail, since a battery in which an energy source is stored or a harvesting unit capable of producing an energy source is required, the weight and size of the device cannot be reduced below a certain level, causing discomfort to a wearer when the wearer moves, while wearing the device, and it may also be difficult for the wearer to wear the device for a long time.

In addition, the conventional electrical stimulation devices have a limited structure to be mounted on any one of various parts of the body (neck, trunk, arm, hand, leg, foot) having different structures, utilization thereof is limited to a specific part for which the design accommodates.

RELATED ART DOCUMENT

Patent Document

Patent document 1: Korean Patent Laid-Open Publication No. 10-2020-0079426

SUMMARY

An exemplary embodiment of the present disclosure is directed to providing a clothing for electrical stimulation that may apply enhanced electrical stimulation to a user's body without a separate power source.

In one general aspect, a clothing for electrical stimulation includes: a main body including a first clothing region clothing a user's sole and a second clothing region worn on a body part other than the user's sole; a first conductor located on an inner surface of the main body and disposed to be in contact with the user's body; and a second conductor electrically connected to the first conductor and located on an outer surface of the main body.

The first conductor and the second conductor may be located in the second clothing region.

The first conductor may be located in the second clothing region, and the second conductor may be located in the first clothing region to come into contact with a ground surface according to a movement of the user.

The first clothing region and the second clothing region may be integrally connected to each other.

The first conductor and the second conductor may be electrically connected to each other by an internal line, and both ends of the internal line may be connected to the first conductor and the second conductor and extend through an inside of the main body.

A thickness of the first clothing region may be thicker than a thickness of the second clothing region.

The first clothing region and the second clothing region may each be a fabric.

The first clothing region and the second clothing region may each have a fiber density of 0.1 to 30 g/cm$^2$.

The main body may have insulating properties.

The main body may have a surface resistance value of $3 \times 10^8$ to $5 \times 10^{12} \Omega$ measured by applying a DC voltage of 500±5 V for 60 seconds according to standard ASTM D257.

The main body may be any one or more selected from leggings, a knee protector, an ankle protector, a calf sleeve, a knee growth plate stimulation sleeve, and a sock.

When the main body is leggings, the first conductor may be located on one surface of the second clothing region in contact with any one or two or more body parts selected from the user's stomach, thighs, calves and buttocks.

When the main body is a knee protector, the first conductor may be located on one surface of the second clothing region in contact with the user's knee.

When the main body is an ankle protector, the first conductor may be located on one surface of the second clothing region in contact with the user's ankle.

When the main body is a calf sleeve, the first conductor may be located on one surface of the second clothing region in contact with the user's calf.

When the main body is a sock, the first conductor may be located on one surface of the second clothing region in contact with any one or two or more body parts selected from the user's ankle, calf, and knee.

When the main body is a knee growth plate stimulation sleeve, the first conductor may be located on one surface of the second clothing region in contact with the user's knee.

When the main body is a sock, the first conductor may be located on one surface of the second clothing region in contact with any one or two or more body parts selected from the user's ankle, calf, and knee, and the second conductor may be located in the second clothing region corresponding to a neck portion of the sock.

Other features and aspects will be apparent from the following detailed description and the drawings.

DETAILED DESCRIPTION

If there are no other definitions in technical terms and scientific terms used here, the technical terms and scientific terms have the meanings commonly understood by those skilled in the art to which the present disclosure pertains, and in the following description and accompanying drawings, descriptions of known functions and components that may unnecessarily obscure the subject matter will be omitted.

Also, as used herein, the singular forms used in the specification are intended to include the plural forms as well, unless the context clearly indicates otherwise.

In addition, in the present disclosure, a unit used without special mentioning is based on the weight, and, for example, the unit of % or ratio refers to weight % or weight ratio, and the weight % refers to wt % of any one component of the entire composition in the composition, unless otherwise defined.

In addition, a numerical range used herein includes a lower limit and an upper limit and all values therebetween, increments logically derived from a form and width of a defined range, all values defined therein, and all possible combinations of an upper limit and a lower limit of a numerical range defined in different forms. Unless otherwise defined in the specification of the present disclosure, values outside the numerical range that may occur due to experimental errors or rounding of values are also included in the defined numerical range.

As used herein, the term 'comprising' is an open-ended description having an equivalent meaning to expressions such as 'including', 'containing', 'having' or 'characterized', and elements, materials, or processes not listed in addition are not excluded.

Since an electrical stimulation device of the related art requires a battery in which an energy source is stored or a harvesting unit capable of producing an energy source, the weight and size of the device cannot be reduced below a certain level, which causes discomfort to a wearer when the wearer moves, while wearing the device, and it may also be difficult for the wearer to wear the device for a long time.

The present applicant has noted that water is a very effective liquid dielectric and most living organisms contain a large amount of water (70-80% of body weight) and confirmed that an object itself containing a large amount of water, such as a living organism, may act as a medium capable of transmitting (propagating) microscopic energy with almost no loss due to a dielectric phenomenon.

With this confirmation, the applicant has recognized and noticed that an electrification phenomenon occurs on a surface of all animals that are substantially present due to contact between an animal and a material (non-living body), a material provided to be in contact with an animal and a material, or an animal and an animal and that an electric field in the form of an alternating current (AC) (triboelectric effect) is generated in living animals as electrical equilibrium changes due to a change in contact inevitably entailed during a contact process.

Accordingly, the applicant has developed an electrical stimulation device capable of generating microscopic electrical stimulation without a connection of an external power source using a microextrinsic AC current (extrinsic AC current: microextrinsic AC current electric field based on a triboelectric generated region), which is inevitably generated in animals including humans due to the triboelectric effect, and a microextrinsic AC electric field that propagates (transfers) from within an animal (including the epidermis) through dielectric polarization due to moisture contained in animals.

The electrical stimulation device proposed by the present applicant basically has a structure based on three independent components: an electrode disposed to contact the skin, an electrode disposed not to contact the skin, and a connecting member connecting the two electrodes.

The present applicant pays attention to the more practical use for commercialization of the electrical stimulation device, and as a result of conducting various studies, the present applicant filed the present disclosure by confirming that relatively strong electrical stimulation may be directly transmitted to the user through the microcurrent generated according to a user's movement when applied to a clothing worn by the user, particularly, a clothing applied to the lower body of the user's body.

A clothing for electrical stimulation according to the present disclosure includes a main body including a first clothing region clothing a user's sole and a second clothing region worn on a body part other than the user's sole; a first conductor located on an inner surface of the main body and disposed to be in contact with the user's body; and a second conductor electrically connected to the first conductor and located on an outer surface of the main body, and such a clothing may apply electrical stimulation to a user not only during an exercise of the user who wears the clothing but also through simple daily movements. Accordingly, the user wearing the clothing may apply electrical stimulation to his/her body only by wearing the clothing, thereby enhancing the effect of beauty, exercise, and muscle treatment without special intense exercise. In addition, when the user does intense exercise by wearing the clothing for electrical stimulation according to the present disclosure, the exercise effect may be further maximized, thereby exhibiting the effect of strengthening the body of the athletes.

Hereinafter, the clothing for electrical stimulation of the present disclosure will be described in detail with reference to the accompanying drawings.

Figure 1:
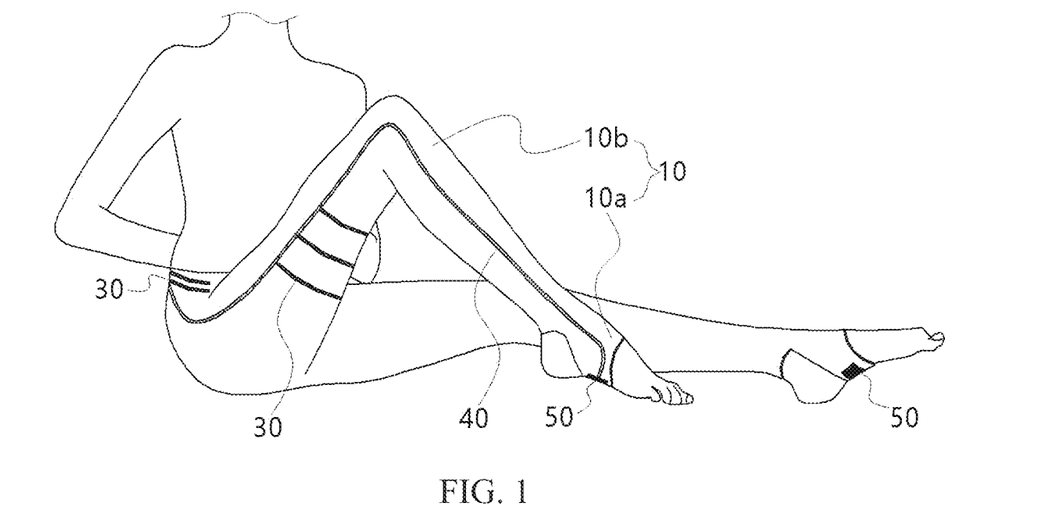
FIG. 1 is a perspective view showing a state in which a user wears a clothing for electrical stimulation according to a first exemplary embodiment of the present disclosure.
Figure 2:
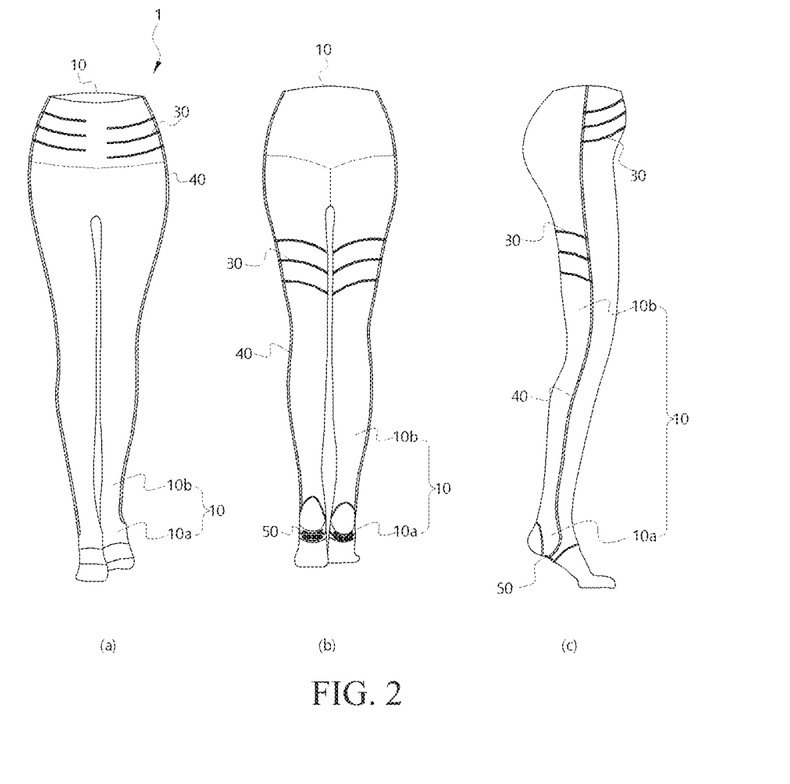
FIG. 2 is a front view, a rear view, and a side view of the clothing for electrical stimulation shown in FIG. 1.

FIGS. 1 to 2 show a user wearing a clothing for electrical stimulation according to an exemplary embodiment of the present disclosure.

Referring to FIGS. 1 to 2, a clothing 1 for electrical stimulation of the present disclosure includes a main body 10 including a first clothing region 10a clothing a user's sole and a second clothing region 10b worn on a body part other than the user's sole, a first conductor 30 located on an inner surface of the main body and disposed to be in contact with the user's body, and a second conductor 50 electrically connected to the first conductor 30 and located on an outer surface of the main body 10.

Figure 3:
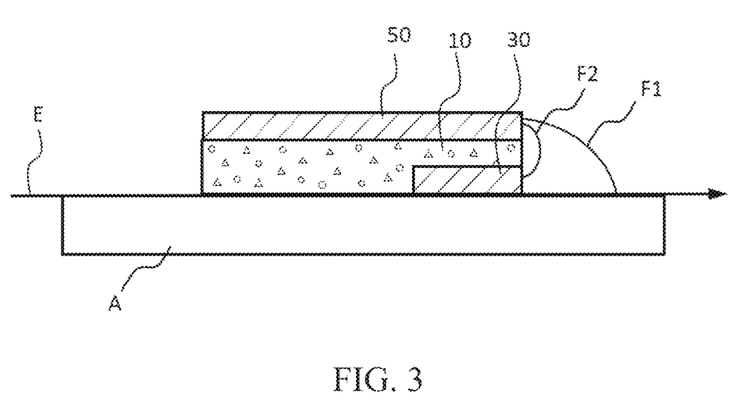
FIG. 3 is a schematic diagram schematically illustrating the clothing for electrical stimulation shown in FIG. 1.

Since the user's body, i.e., a human body, is made up of 70 to 80 percent of the polar molecule water, a dielectric phenomenon occurs, and as shown in FIG. 3, a current E flows and a first electric field F1 is formed. At this time, the first conductor 30 and the second conductor 50 have a potential difference due to an electric field generated in the human body. When the two conductors have a potential difference, current in the form of an AC is generated between the two conductors, forming a second electric field F2 so that the human body is stimulated by the second electric field F2. Accordingly, since it is possible to apply a certain electric stimulation to a local body part in contact with the first conductor 30, more cells may be activated, thereby maximizing an exercise effect.

As shown in FIGS. 1 and 2, the first conductor is located in the second clothing region, and the second conductor may be located in the first clothing region, i.e., on an outer surface of the sole of the user's foot, to come into contact with a ground surface according to the user's movement. In such a clothing for electrical stimulation, when the user wearing the clothing brings the sole of the foot into contact with the ground, the second conductor is grounded so that a potential difference with the first conductor electrically connected thereto increases and stronger electrical stimulation may be provided to the first conductor, thereby further maximizing the cosmetic, exercise, and muscle treatment effects of electrical stimulation.

Alternatively, the first conductor and the second conductor may be located in the second clothing region. Such a clothing for electrical stimulation may apply appropriate electrical stimulation when worn by an athlete who does relatively intense exercise, which may maximize the athlete's exercise effect.

Specifically, the main body 10 includes the first clothing region 10a worn on the user's sole to surround the user's sole and the second clothing region 10b worn on a user's body part as an electrical stimulation target excluding the sole, as a part in which the subject maintains a shape applicable to the human body. The main body 10 includes the first clothing region 10a and the second clothing region 10b, and the shape and form are not particularly limited as long as it may be worn on the user's body. Specifically, the main body 10 may be both a top worn on an upper body and bottoms worn on a lower body, but it may be useful in the efficiency of generating electrical stimulation to be worn on the lower body, which has relatively more movement than the upper body in the user's body. More specifically, as shown in the drawings, the main body 10 may be bottoms for exercise, that is, leggings 10 formed with a foot ring, and the main body 10 may be a knee protector, an ankle protector, a calf sleeve, a knee growth plate stimulation sleeve, and socks, including the first clothing region 10a and the second clothing region 10b.

The main body 10 may have insulating properties, which improves the potential difference between the first conductor 30 and the second conductor 50, and further increases electrical stimulation applied to the user's body through the first conductor 30.

Specifically, the main body 10 may have a resistance value of $1 \times 10^8 \Omega$ or greater, or $3 \times 10^8$ to $5 \times 10^{12} \Omega$, or $5 \times 10^{10}$ to $1 \times 10^{12} \Omega$ measured by applying a DC voltage of 500±5 V for 60 seconds according to standard ASTM D257, and having an insulating characteristic within the above range, the main body 10 may strengthen the electrical stimulation applied to the user's body through the first conductor 30.

The first clothing region 10a of the main body 10 is worn to cover the user's sole and is not limited thereto as long as the second conductor 50 to be described later covers the user's sole so that it may be easily located on the user's sole. As an example, as shown in the drawings, the first clothing region 10a may be in the shape of a foot ring that surrounds the user's instep and the sole of the foot, but alternatively, the first clothing region 10a may be in the shape of socks (with foot) surrounding the whole foot.

The second clothing region 10b is worn on the user's electrical stimulation target body part, and is not limited as long as it may be worn on the user's body. In the main body 10, the second clothing region 10b may refer to a region excluding the first region covering the user's sole. Specifically, as shown in FIGS. 1 to 2, when the main body 10 is leggings, the sole of the foot ring portion of the leggings may be the first clothing region 10a, and the remaining portions may be the second clothing region 10b.

The first clothing region 10a and the second clothing region 10b may be provided separately so that the user may wear them, separately, if necessary. Alternatively, as shown in FIGS. 1 to 2, the first clothing region 10a and the second clothing region 10b may be connected to each other as an integral type. When the first clothing region 10a and the second clothing region 10b are integrated, the first conductor 30 and the second conductor 50 to be described later may be easily electrically connected, and it can be easily worn by the subject so that preference may be higher.

In some embodiments, the first clothing region 10a and the second clothing region 10b are each fabric which may increase the user's wearing comfort. In particular, the first clothing region 10a and the second clothing region 10b may each have a fiber density of 0.1 to 30 $g/cm^2$, specifically 0.5 to 20 $g/cm^2$, and more specifically 1 to 10 $g/cm^2$, and may be useful in terms of insulating properties.

As described above, since it is useful for the main body 10 to have insulating properties, it is useful for the first clothing region 10a and the second clothing region 10b also to have insulating properties, and even if the main body 10 has the same insulating properties, as the main body 10 is thicker, the main body 10 may have improved insulating ability in reinforcing electrical stimulation, but the main body 10 may be formed in the thickness of a fabric commonly known for clothing so as not to interfere with a movement of the user.

However, it is possible to make the main body 10 have higher insulating properties by adjusting the thickness of the first clothing region 10a, which has less influence on the movement of the user. Specifically, the thickness of the first clothing region 10a may be greater than the thickness of the second clothing region 10b by 1.1 to 5 times, or 1.5 to 3 times, to increase insulating properties, without interfering with the movement of the user.

The first conductor 30 and the second conductor 50 are respectively located on the inner and outer surfaces of the main body described above and are spaced apart from each other based on the center of the main body. A distance between the two conductors is not particularly limited, and as the distance between the first conductor 30 and the second conductor 50 increases, the intensity of electrical stimulation may be strengthened.

In this case, the distance between the two conductors may refer to the shortest distance between the two conductors.

The first conductor 30 is located on one surface of the aforementioned second clothing region 10b to be in contact with the user's body.

The first conductor 30 is not limited as long as it contains a conductive material having conductivity. In some embodiments, a surface of the first conductor 30 is flat so as not to inflict an injury to the user's body on one surface of the second clothing region 10b in contact with the user's body. In addition, as shown in the drawings, the first conductor 30 may be provided as a line-shaped pattern having a constant length, but is not limited thereto, and may be provided in various shapes such as a sphere, a polygon, and the like, and a size thereof is also not limited. However, the first conductor 30 is of a thin film type so as not to cause discomfort to the user when the first conductor 30 comes into contact with the user, and specifically, the first conductor 30 may be formed to have a thickness of 2 mm or less.

In addition, the first conductor 30 may be located anywhere in the second clothing region 10b at a position corresponding to the user's body requiring stimulation, and may be located at positions corresponding to two or more body parts.

The second conductor 50 may be electrically connected to the first conductor 30, may be located on a surface opposite to the one surface of the first clothing region 10a in contact with the user's sole, and may be in contact with the ground according to a user's movement. Accordingly, the clothing for electrical stimulation of the present disclosure may be grounded by the second conductor 50, and as the potential difference between the first conductor 30 and the second conductor 50 becomes very large, a greater electrical stimulation may be transmitted to the user's body in contact with the first conductor 30.

Alternatively, the second conductor 50 may be located in the second clothing region 10b as described above. As such, when the second conductor 50 is located in the second clothing region 10b, a potential difference between the first conductor 30 and the second conductor 50 may be reduced, compared to when the second conductor 50 is located in the first clothing region 10a, weakening electrical stimulation transmitted to the first conductor 30, but when a relatively intense exercise such as soccer, basketball, ice hockey, or American football is performed, the movement is not disturbed and sufficient electrical stimulation may be applied to maximize an exercise effect.

That is, in order to generate strong electrical stimulation only with light exercise such as jogging, yoga, pilates, etc., which are not vigorous, or daily movements, the second conductor 50 may be located in the first clothing region 10a, and it may be useful for the second conductor 50 to be located in the second clothing region 10b in order to generate an appropriate electrical stimulation when playing sports such as soccer, basketball, and the like, with intense movement.

The second conductor 50 is electrically connected to the first conductor 30, and the second conductor 50 is also not limited as long as it contains a conductive material having conductivity, and a surface of the second conductor 50 may be flat not to injure the user. Also, the second conductor 50 may be provided in various shapes like the first conductor 30. When the second conductor 50 is located in the first clothing region 10a, the second conductor 50 may apply electrical stimulation having the same magnitude as long as it comes into contact with the ground regardless of the size. Accordingly, the size of the second conductor 50 is not limited, but it may be formed over the entire sole of the sole to relatively increase a groundable area. Meanwhile, when the second conductor 50 is located in the second clothing region 10b, the size is not particularly limited. Specifically, the second conductor 50 may have the same size as the first conductor 30 or may be smaller than the first conductor 30. The second conductor may be formed to be larger than the first conductor 30 to enhance the electrical stimulation strength.

In addition, the second conductor 50 may be in a thin film type so as not to cause inconvenience to the user, and may have a thickness of 2 mm or less, but is not limited thereto.

In addition, although the second conductor 50 may be located on an outer surface of the main body 10 as described above, it may be covered by a protective member to be protected from an external environment. The protective member (not shown) is not limited as long as it has insulating properties and protects the second conductor 50. Specifically, the protective member may be formed of the same material as the main body 10 and integral with the main body.

The second conductor 50 and the first conductor 30 may be electrically connected to each other by a connecting means having conductivity, such as a generally known electric wire or conductive thread, and the connecting means is not limited as long as it may electrically connect the second conductor and the first conductor.

For example, as shown in the drawings, the first conductor 30 and the second conductor 50 may be electrically connected to each other through the internal line 40. The internal line 40 is also formed of a conductive material, and both ends of the internal line 40 may be connected to the first conductor 30 and the second conductor 50 and may extend through the inside of the main body 10. This internal line 40 electrically connects the first conductor 30 and the second conductor 50 but is not exposed to the external environment, thereby suppressing noise occurrence of electrical stimulation caused by external factors, to form more stable and uniform electrical stimulation, and thus, the first conductor 30 and the second conductor 50 may be stably electrically connected to each other even with a vigorous movement of the user.

Alternatively, the first conductor 30 and the second conductor 50 may be electrically connected to each other by one surface of the main body 10 in contact with the user or an external line exposed to the outside.

The first conductor 30, the second conductor 50, the internal line 40, and the external line (not shown) described above may include a conductive material as described above, and the conductive material may include a metal, a conductive polymer, a conductive carbon material, a conductive organic material, a conductive oxide, or a combination thereof. In this case, the combination may also include a composite material such as a metal and a conductive carbon material, a conductive organic material and a conductive carbon material, and a metal and a conductive organic material.

Examples of the conductive carbon material may include, but are not limited to, carbon fibers, activated carbon, carbon nanotubes, graphite, carbon black, graphene, and combinations thereof.

The conductive organic material may include, for example, a conductive polymer, and the conductive polymer may be any one or two or more selected from polyacetylene, polyaniline, polypyrrole, and polythiophene, but is not limited thereto. As a practical example, the conductive polymer may include polyacetylene (PA), polyaniline (PANI), polypyrrole (PPy), polythiophene (PT), and poly(3,4-ethylenedioxythiophene) (PEDOT), polyisothianaphthene (PITN), polyphenylene vinylene (PPV), polyphenylene (PPE), polyphenylene sulfide (PPS), and polysulfur nitride (PSN), etc., but is not limited thereto.

As the metal itself is a very good conductor, one or more metals selected from the group consisting of alkali metals, alkaline earth metals, transition metals, post-transition metals, or alloys thereof may be sufficient. However, since an upper surface of a substrate on which the first conductor 30 is located may be a region in which the subject is active, and since the upper surface is in direct contact with the body of the subject, the metal may be a metal having bio-stability upon skin contact, such as copper, gold, silver, stainless steel, or aluminum, for more secure use stability.

The conductive oxide may include transparent conductive oxides commonly used as transparent electrodes, and examples of the transparent conductive oxide may include fluorine doped tin oxide (FTO), indium doped tin oxide (ITO), Ga doped ZnO (GZO), and Al doped ZnO (AZO), ZnO, $SnO_2$, $TiO_2$, and the like, but is not limited thereto.

As described above, FIGS. 1 to 2 show a clothing for electrical stimulation according to the first exemplary embodiment of the present disclosure, that is, a clothing for electrical stimulation in which the main body 10 is leggings.

Referring to FIGS. 1 and 2, the main body 10 of the present disclosure may be leggings including an integral foot ring. In this case, the foot ring may be the first clothing region 10a, and the other regions may be the second clothing region 10b.

As described above, the second conductor 50 may be located in the second clothing region 10b, that is, at the sole of the foot in contact with the ground of the ring, and the first conductor 30 may be located on one surface of the second clothing region 10b in contact with any one or two or more body parts selected from the stomach, thighs, calves, and buttocks.

As shown in FIGS. 1 to 2, the clothing for electrical stimulation using leggings as the main body 10 has no objection to existing leggings users, and may provide a very high preference by allowing a higher exercise effect.

Figure 4:
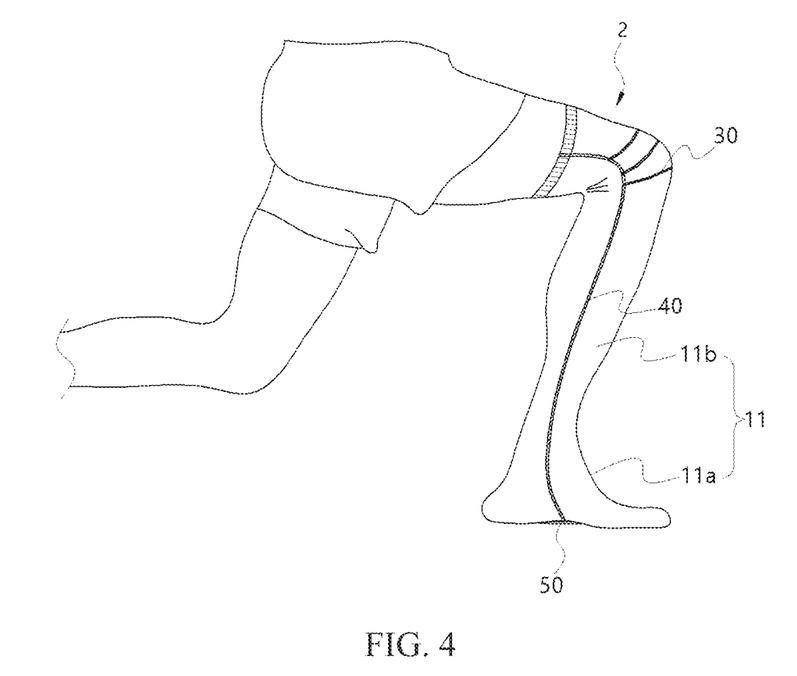
FIGS. 4 to 9 are schematic views respectively showing the clothing for electrical stimulation according to second to seventh exemplary embodiments of the present disclosure.

In addition, FIG. 4 shows a clothing 2 for electrical stimulation according to a second exemplary embodiment of the present disclosure, that is, a clothing 2 for electrical stimulation in which the main body 11 is a knee growth plate stimulation sleeve.

Referring to FIG. 4, the main body 11 may be a knee growth plate stimulation sleeve. In this case, the first clothing region 11a and the second clothing region 11b may be integrally formed, a sock portion covering the foot may be the first clothing region 11a, and the other regions may be the second clothing region 11b.

As described above, the second conductor 50 may be located in the first clothing region 11a, that is, at the sole of the sock in contact with the ground, and the first conductor 30 may be located on one surface of the second clothing region 11b in contact with the user's knee.

Such a clothing for electrical stimulation may maximize the growth plate stimulation effect by intensively applying electrical stimulation to the user's knee.

Unlike that illustrated in FIG. 4, the second conductor 50 may be located in the second clothing region 11b of the main body 11.

Figure 5:
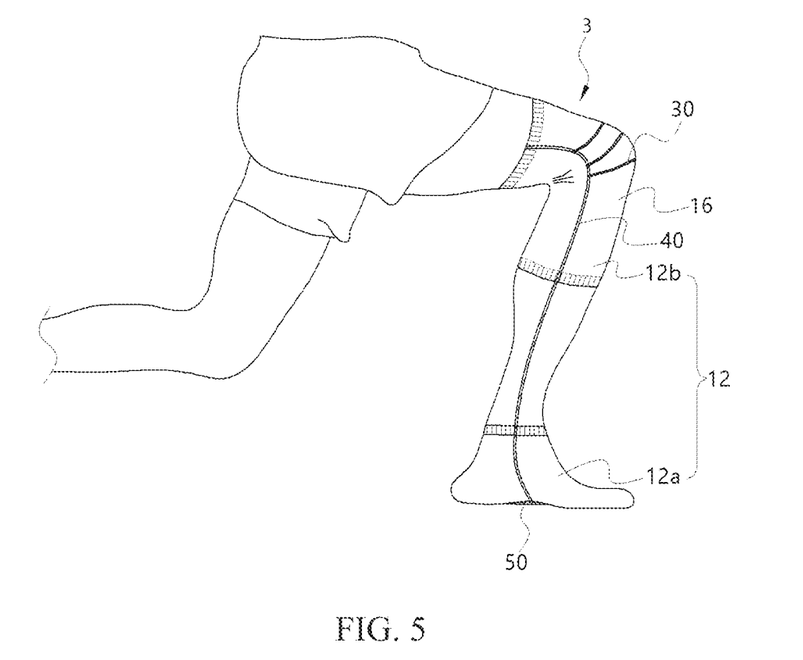

FIG. 5 shows a clothing 3 for electrical stimulation according to a third exemplary embodiment of the present disclosure, that is, a clothing 3 for electrical stimulation in which a main body 12 is a knee protector.

Referring to FIG. 5, the main body 12 may be a knee protector. At this time, a first clothing region 12a and a second clothing region 12b are provided separately, a sock portion covering the foot is the first clothing region 12a, and a region covering the knee is the second clothing region 12b. As such, the separately wearable first clothing region 12a and the second clothing region 12b may also be interconnected by the internal line 40, but the internal line 40 may be covered.

As described above, the second conductor 50 may be located in the first clothing region 12a, that is, at the sole of the sock portion, and the first conductor 30 may be located on one surface of the clothing region 12b in contact with the user's knee.

Such a clothing for electrical stimulation may apply electrical stimulation intensively to the user's knee.

Unlike that illustrated in FIG. 5, the second conductor 50 may be located in the second clothing region 12b of the main body 12.

Figure 6:
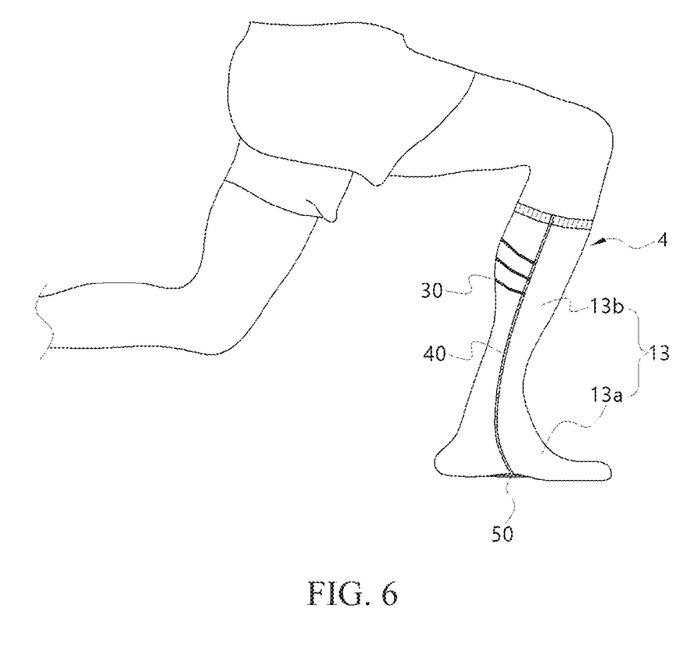

FIG. 6 shows a clothing 4 for electrical stimulation according to a fourth exemplary embodiment of the present disclosure, that is, a clothing 4 for electrical stimulation in which a main body 13 is a calf sleeve.

Referring to FIG. 6, the main body 13 may be a sleeve for stimulating the calf. In this case, a first clothing region 13a and a second clothing region 13b may be integrally formed, a sock portion covering the foot may be the first clothing region 13a, and the other regions may be the second clothing region 13b.

As described above, the second conductor 50 may be located in the first clothing region 13a, that is, at the sole of the sock portion, and the first conductor 30 may be located on one surface of the second clothing region 13b in contact with the user's calf.

The clothing 4 for electrical stimulation may maximize the muscle stimulation effect by intensively applying electrical stimulation to the user's calf.

Unlike that illustrated in FIG. 6, the second conductor 50 may be located in the second clothing region 13b of the main body 13.

Figure 7:
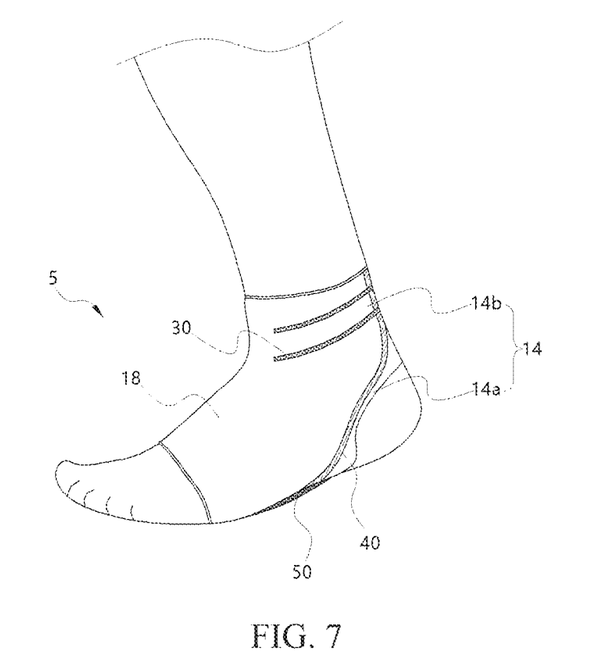

FIG. 7 shows a clothing 5 for electric stimulation according to a fifth exemplary embodiment of the present disclosure, that is, a clothing 5 for electrical stimulation in which a main body 14 is an ankle protector.

Referring to FIG. 7, the main body 14 may be an ankle protector. At this time, a first clothing region 14a and a second clothing region 14b may be integrally formed, and a foot ring portion covering the instep and sole of the foot is the first clothing region 14a, and a region other than region covering the foot may be the second clothing region 14b.

As described above, the second conductor 50 may be located in the first clothing region 14a, that is, at the sole of the foot ring in contact with the ground, and the first conductor 30 may be located on one surface of the second clothing region 14b in contact with the user's ankle.

Such a clothing 5 for electrical stimulation may apply electrical stimulation intensively to the user's ankle.

Unlike that illustrated in FIG. 7, the second conductor 50 may be located in the second clothing region 14b of the main body 14.

Figure 8:
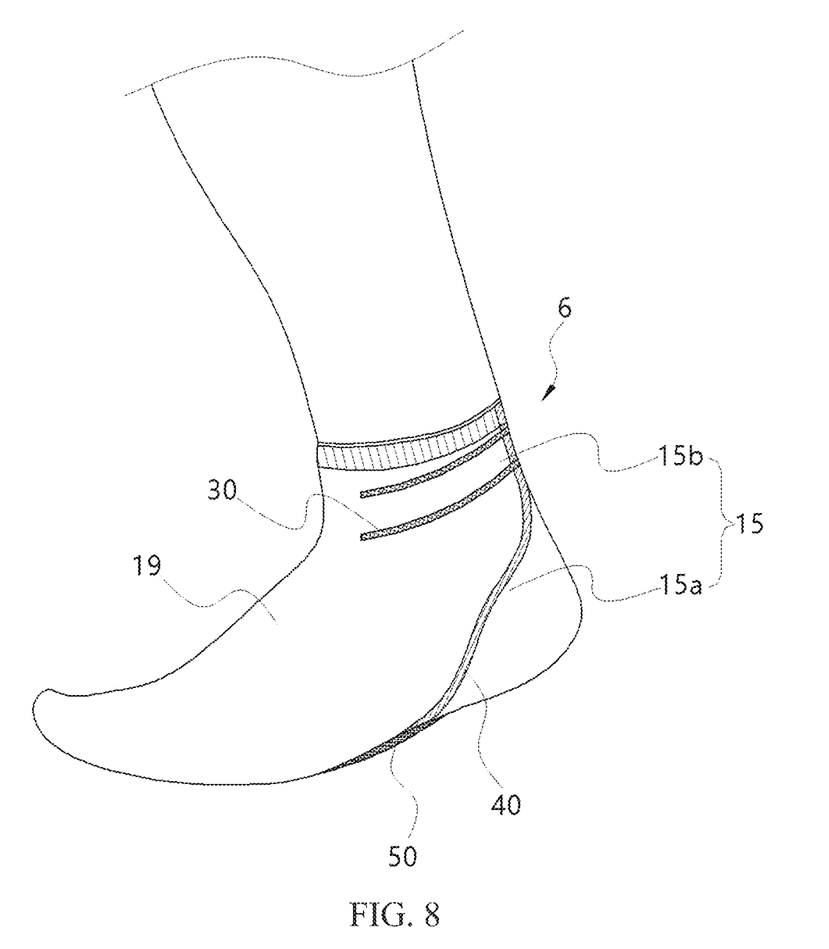

FIG. 8 shows a clothing 6 for electrical stimulation according to a sixth exemplary embodiment of the present disclosure, that is, a clothing 6 for electrical stimulation in which a main body 15 is a sock.

Referring to FIG. 8, the main body 15 may be a sock. At this time, a first clothing region 15a and a second clothing region 15b may be integrally formed, a portion covering the instep and sole of the foot is the first clothing region 15a, and a region other than the region covering the foot is the second clothing region 15b.

As described above, the second conductor 50 may be located in the first clothing region 15a, that is, at the sole of the foot in contact with the ground, and the first conductor 30 may be located on one surface of the second clothing region 15b in contact with the user's ankle.

Such a clothing for electrical stimulation may apply electrical stimulation intensively to the user's ankle.

Figure 9:
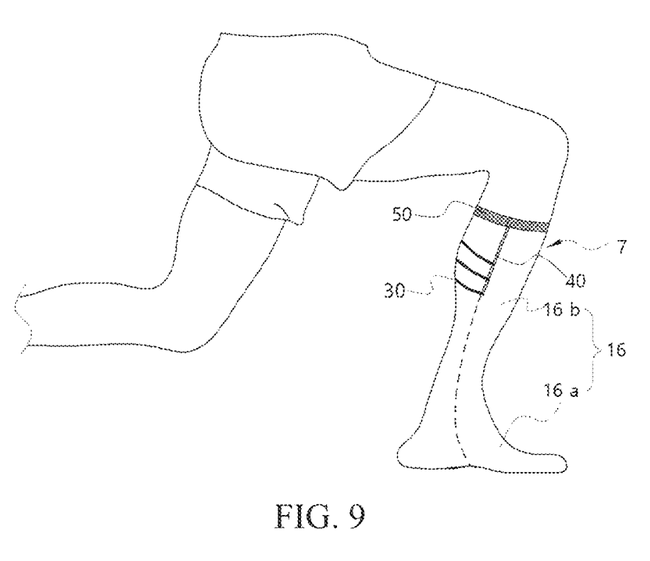

As shown in the drawings, such socks may have a relatively short length, but alternatively, as shown in FIG. 9, the socks may be long socks.

FIG. 9 shows a clothing 7 for electrical stimulation according to a seventh exemplary embodiment of the present disclosure, that is, a clothing 7 for electrical stimulation in which main body 16 is a sock and the first and second conductors 30 and 50 are located in the second clothing region 16b.

Referring to FIG. 9, the first conductor 30 and the second conductor 50 may be respectively located on an inner surface and an outer surface of the second clothing region 16b of the main body 16, respectively. In particular, the second conductor 50 may be located in the main body 16, that is, at the neck portion of the sock. The neck portion of the sock may be formed to be thicker than other portions of the sock, and as described above, the insulation of the main body is high so that a relatively strong electrical stimulation may be applied.

Such a clothing for electrical stimulation may apply an appropriate electrical stimulation without interfering with a movement even during intense exercise, so that when worn by athletes performing intense exercise, a more excellent exercise strengthening effect may be obtained.

In addition, in the case of players with a lot of foot and leg exercise, such as soccer, there is a very high possibility of suffering various injuries such as sprains, fractures, muscle pain and ligament rupture, and it takes more than a certain time to recover from the injury.

When the clothing for electrical stimulation according to the present disclosure is worn, faster recovery may be made by applying electrical stimulation to the injured area, than when not wearing it. In particular, as the user's movement is generally concentrated on the feet, when the main body of the clothing for electrical stimulation is worn by the user as a sock, a lot of friction may be generated with the skin and the ground and a greater amount of friction electricity may be generated due to elasticity of the socks. Accordingly, strong electrical stimulation may be applied, thus having a very fast recovery effect through rehabilitation exercise from an injury.

Although a relatively long sock is shown in FIG. 9, the main body may be a relatively short sock as shown in FIG. 8.

Figure 10:
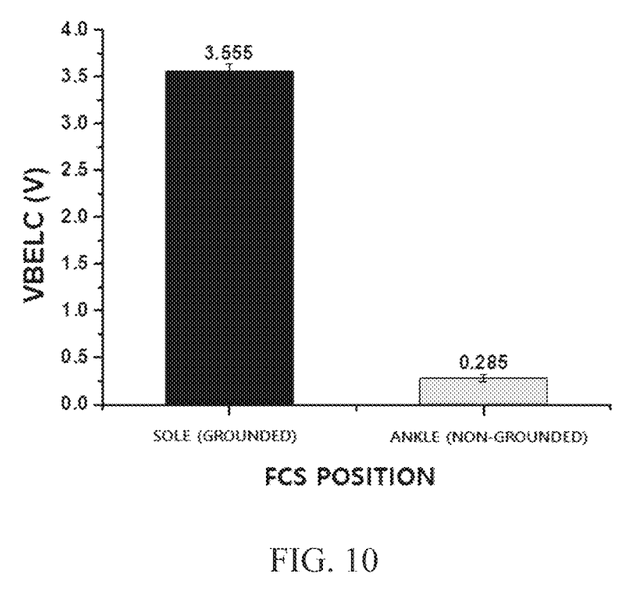
FIGS. 10 to 13 are experimental results showing an electrical stimulation effect of a clothing for electrical stimulation according to an exemplary embodiment of the present disclosure.

FIG. 10 is a graph showing a comparison graph of electrical stimulation intensity according to positions of the second conductor 50.

Specifically, as shown in FIG. 1, leggings in which the second conductor 50 is located on the user's sole and comparative example leggings in which the second conductor 50 is located at the ankle unlike in FIG. 1, are provided, and voltages applied to the first conductor 30 when the same user wearing both leggings moves in the same manner were measured and results thereof are shown.

Referring to FIG. 10, it can be seen that, as the leggings of the present disclosure are grounded with the ground, 10 times or more electrical stimulation may be applied compared to the non-grounded leggings.

Figure 11:
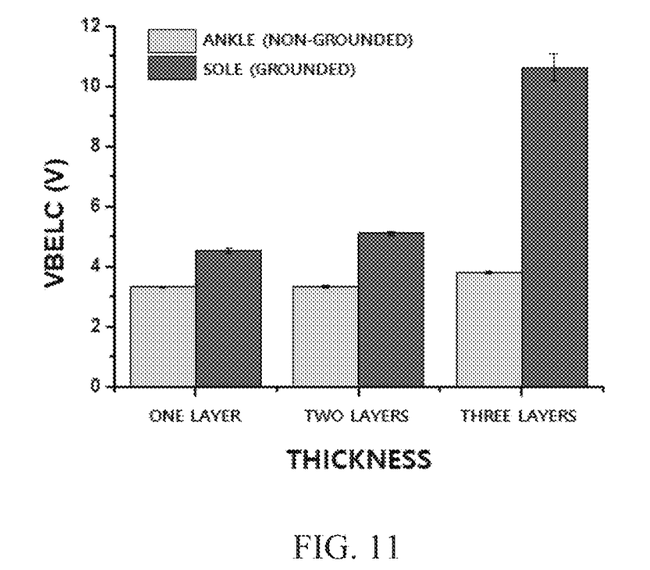

FIG. 11 is a graph showing the comparison of electrical stimulation intensity according to the thickness of the main body.

Specifically, after thickness of the main body of the leggings illustrated in FIG. 1 is adjusted by laminating one layer, two layers, and three layers, a voltage applied to the first conductor is measured when the same user wearing the leggings of each thickness moves in the same manner, and results thereof are shown.

Referring to FIG. 11, it can be seen that as the thickness increases, insulating properties of the main body increases, so that a stronger stimulus may be applied.

Figure 12:
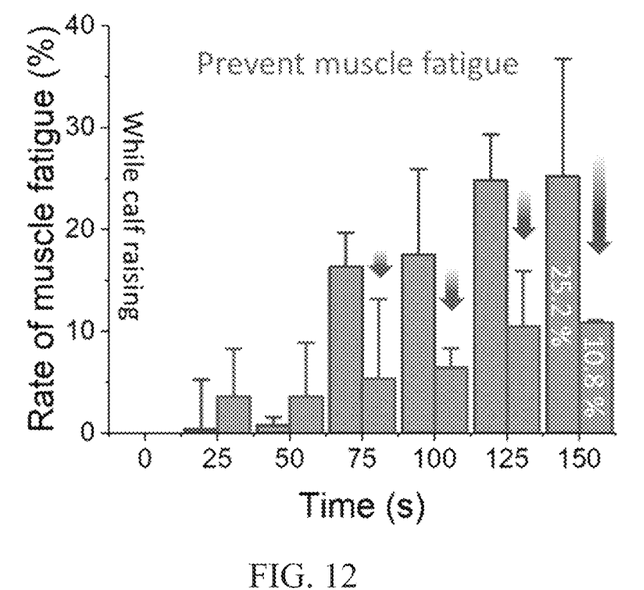

FIG. 12 is a graph showing muscle fatigue measured after the same user wears the calf sleeve shown in FIG. 5 and the general sleeve in which the second conductor is not located on the sole of the foot.

For muscle fatigue, the user wearing the calf sleeve shown in FIG. 7 under room temperature (24±2)° C. and regular humidity (40±3)%RH performed 5 sets of 10 repetitions of calf raises and then an electromyogram (EMG) over time was measured. The presence or absence of electrical stimulation applied to the human body was checked through an oscilloscope, and muscle fatigue was evaluated based on a change in a median frequency of an EMG signal before and after exercise. Thereafter, after the same user took a sufficient rest, the user wore a general sleeve and muscle fatigue was measured in the same manner as that of the aforementioned method for measuring muscle fatigue.

Referring to FIG. 12, it can be seen that the clothing for electrical stimulation of the present disclosure reduces muscle fatigue by more than 50% compared to the general clothing when worn.

Figure 13:
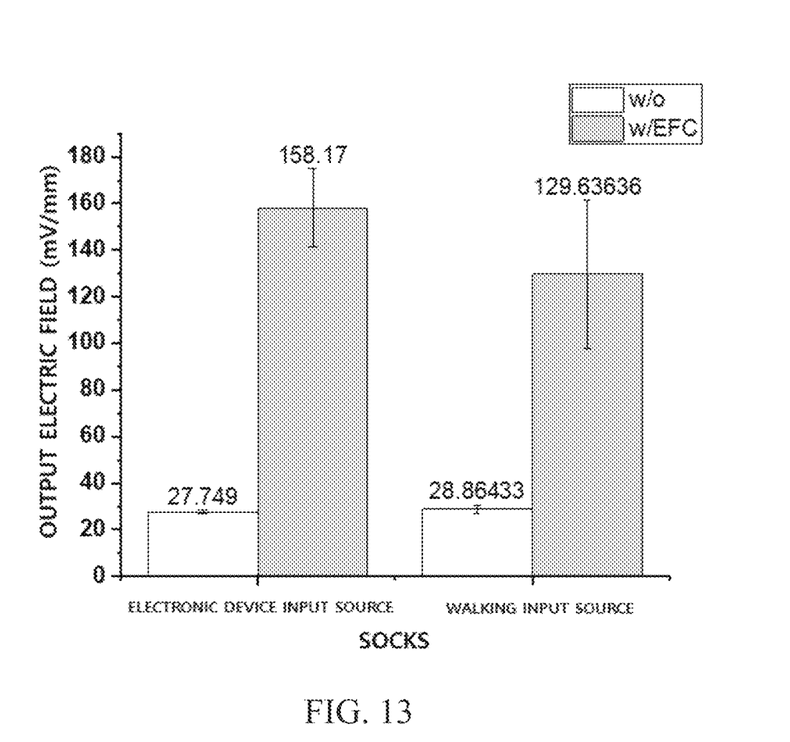

FIG. 13 is a view of measuring the magnitude of electrical stimulation applied to the human body after wearing a clothing for electrical stimulation having a structure in which a first conductor and a second conductor are located in a second clothing region, as shown in FIG. 9.

The result of measuring electrical stimulation presented in FIG. 13 was measured by the following method.

Electrical stimulation measurement method: Two multimeters are prepared and an output electric field (mV/mm) generated in a skin local area was measured with a multimeter (1), and a potential difference V between a skin contact region (first area) and a skin non-contact region (second area) is measured with a multimeter (2). To measure the output electric field (mV/mm), two electrodes of the multimeter (1) are attached to the skin at an interval of 1 mm. In this case, a measurement probe is connected to the skin contact area (first area) of the first conductor that comes into contact with the skin, and a ground probe is attached to the skin at intervals of 1 mm. Then, a potential difference mV measured in the two conductors is divided by the distance (1 mm) between the two electrodes to obtain the output electric field (mV/mm). The potential difference V is measured by connecting the measurement probe of the multimeter (2) to a first region which is the same as the multimeter (1) and connecting the other ground probe to the second conductor region (second region) not in contact with the skin.

During the measurement, a basic noise electric field generated in the human body, without wearing an electrical stimulation article, was measured and a value thereof is shown as "W/O" in the drawing. After measuring the basic noise electric field, the electric stimulation article was worn, and an output electric field and a potential difference were obtained according to the aforementioned method, and a value thereof is shown as "w/EFC (basic)". In addition, the clothing for electrical stimulation having the structure shown in FIG. 9 was worn, an output electric field and a potential difference were obtained according to the aforementioned method, and a value thereof is shown as "w/EFC". At this time, in the case of using energy wasted from an electronic device, an output of each of the multimeters of (1) and (2) was measured by putting a hand on the electronic device, and a measurement value thereof is shown as "electronic device input source". In the case of using energy generated by contact electrification, an output of each of the multimeters (1) and (2) was measured, while walking at a constant speed in place, and a measurement value of (2) is shown as "walking input source".

Referring to FIG. 13, it can be seen that, when energy discarded from electronic devices is used as an input source as well as when energy generated by contact electrification (walking input source) is used as an input source, electrical stimulation can be applied to the human body by the clothing for electrical stimulation.

The clothing according to the present disclosure may apply electrical stimulation to the user's body only by the user's movement without a separate power source.

In addition, the clothing according to the present disclosure may enhance the strength of the electrical stimulation applied to the body of the user wearing the clothing.

Furthermore, the user wearing the clothing according to the present disclosure may enhance the effect of beauty, exercise and muscle treatment.

Hereinabove, although the present disclosure is described by specific matters, exemplary embodiments, and drawings, they are provided only for assisting in the entire understanding of the present disclosure. Therefore, the present disclosure is not limited to the exemplary embodiments. Various modifications and changes may be made by those skilled in the art to which the present disclosure pertains from this description.

Therefore, the spirit of the present disclosure should not be limited to the aforementioned embodiments, as well as all modified equally or equivalently to the aforementioned embodiments are intended to fall within the scope and spirit of the disclosure.

| Detailed Description of Main Elements | |
|---|---|
| 1: clothing for electrical stimulation | 10: main body |
| 30: First conductor | 40: Internal line |
| 50: Second conductor | |

The invention claimed is:

1. A clothing for electrical stimulation, the clothing comprising:
 a main body including a first clothing region clothing a user's sole and a second clothing region worn on a body part other than the user's sole;
 a first conductor located on an inner surface of the main body and disposed to be in contact with the user's body; and
 a second conductor electrically connected to the first conductor and located on an outer surface of the main body;
 wherein the first clothing region and the second clothing region each are a fabric;
 wherein an alternating current (AC), generated between the first conductor in contact with the user's body through an externally induced AC electric field flowing within the body due to the water in the body and the second conductor located on the outer surface of the main body, forms a magnetic field that stimulates the human body and applies electrical stimulation without requiring a separate power source.

2. The clothing of claim 1, wherein the first conductor and the second conductor are located in the second clothing region.

3. The clothing of claim 1, wherein the first conductor is located in the second clothing region, and the second conductor is located in the first clothing region to come into contact with a ground surface according to a movement of the user.

4. The clothing of claim 1, wherein the first clothing region and the second clothing region are integrally connected to each other.

5. The clothing of claim 1, wherein the first conductor and the second conductor are electrically connected to each other by an internal line, and both ends of the internal line are connected to the first conductor and the second conductor and extend through an inside of the main body.

6. The clothing of claim 1, wherein a thickness of the first clothing region is thicker than a thickness of the second clothing region.

7. The clothing of claim 1, wherein the first clothing region and the second clothing region each have a fiber density of 0.1 to 30 $g/cm^3$.

8. The clothing of claim 1, wherein the main body has insulating properties.

9. The clothing of claim 1, wherein the main body has a surface resistance value of $3\times10^8$ to $5\times10^{12}\Omega$ measured by applying a DC voltage of 500±5 V for 60 seconds according to standard ASTM D257.

10. The clothing of claim 1, wherein the main body is any one or more selected from leggings, a knee protector, an ankle protector, a calf sleeve, a knee growth plate stimulation sleeve, and a sock.

11. The clothing of claim 10, wherein, when the main body is leggings, the first conductor is located on one surface of the second clothing region in contact with any one or two or more body parts selected from the user's stomach, thighs, calves, and buttocks.

12. The clothing of claim 10, wherein, when the main body is a knee protector, the first conductor is located on one surface of the second clothing region in contact with the user's knee.

13. The clothing of claim 10, wherein, when the main body is an ankle protector, the first conductor is located on one surface of the second clothing region in contact with the user's ankle.

14. The clothing of claim 10, wherein, when the main body is a calf sleeve, the first conductor is located on one surface of the second clothing region in contact with the user's calf.

15. The clothing of claim 10, wherein, when the main body is a sock, the first conductor is located on one surface of the second clothing region in contact with any one or two or more body parts selected from the user's ankle, calf, and knee.

16. The clothing of claim 10, wherein, when the main body is a knee growth plate stimulation sleeve, the first conductor is located on one surface of the second clothing region in contact with the user's knee.

17. The clothing of claim 10, wherein, when the main body is a sock, the first conductor is located on one surface of the second clothing region in contact with any one or two or more body parts selected from the user's ankle, calf, and knee, and the second conductor is located in the second clothing region corresponding to a neck portion of the sock.

* * * * *